United States Patent
Mozdzierz et al.

(10) Patent No.: US 9,016,547 B2
(45) Date of Patent: Apr. 28, 2015

(54) EEA TILT TOP ANVIL WITH RATCHET/LOCKING MECHANISM

(75) Inventors: Patrick Mozdzierz, Glastonbury, CT (US); Lee Ann Olson, Wallingford, CT (US)

(73) Assignee: Covidien LP, Mansfield, MA (US)

( * ) Notice: Subject to any disclaimer, the term of this patent is extended or adjusted under 35 U.S.C. 154(b) by 388 days.

(21) Appl. No.: 13/281,899

(22) Filed: Oct. 26, 2011

(65) Prior Publication Data

US 2013/0105544 A1    May 2, 2013

(51) Int. Cl.
*A61B 17/04* (2006.01)
*A61B 17/10* (2006.01)
*A61B 17/115* (2006.01)
*A61B 17/072* (2006.01)

(52) U.S. Cl.
CPC ... *A61B 17/1155* (2013.01); *A61B 2017/07257* (2013.01)

(58) Field of Classification Search
CPC .................. A61B 17/0644; A61B 2017/07257
USPC .............. 227/179.1, 19, 175.1; 606/151–153, 606/142, 219, 37
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev |
| 3,638,652 A | 2/1972 | Kelley |
| 3,771,526 A | 11/1973 | Rudie |
| 4,198,982 A | 4/1980 | Fortner et al. |
| 4,207,898 A | 6/1980 | Becht |
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |

(Continued)

FOREIGN PATENT DOCUMENTS

| | | |
|---|---|---|
| CA | 908529 | 8/1972 |
| CA | 1136020 A | 11/1982 |

(Continued)

OTHER PUBLICATIONS

European Search Report dated Feb. 18, 2013 from corresponding EP Application No. 12186167.8 (4 pgs.).

*Primary Examiner* — Robert Long (57) ABSTRACT

A tilt anvil assembly is disclosed which includes a center rod and a head assembly pivotally mounted to the center rod. The head assembly includes a housing, a post and an anvil plate. The head assembly is pivotally secured to the center rod and pivotal in relation to the center rod in discrete steps between a non-tilted position and a fully tilted position via a plurality of partially tilted positions. The head assembly is configured to maintain a partially tilted position.

14 Claims, 9 Drawing Sheets

(56) References Cited

U.S. PATENT DOCUMENTS

| | | |
|---|---|---|
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,622 A | 1/1990 | Green et al. |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,381,943 A * | 1/1995 | Allen et al. ............... 227/177.1 |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,673,840 A * | 10/1997 | Schulze et al. ............. 227/175.1 |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balázs et al. |
| 6,264,086 B1 | 7/2001 | McGuckin, Jr. |
| 6,269,997 B1 | 8/2001 | Balázs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |

(56) References Cited

U.S. PATENT DOCUMENTS

| | | |
|---|---|---|
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 * | 4/2009 | Aranyi ................. 227/176.1 |
| 7,527,185 B2 | 5/2009 | Harari et al. |
| 7,537,602 B2 | 5/2009 | Whitman |
| 7,546,939 B2 * | 6/2009 | Adams et al. ............. 227/180.1 |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,798,386 B2 * | 9/2010 | Schall et al. ................ 227/176.1 |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Fuchs et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |

(56) References Cited

U.S. PATENT DOCUMENTS

| | | | |
|---|---|---|---|
| 8,028,885 B2 | 10/2011 | Smith et al. | |
| 8,038,046 B2 | 10/2011 | Smith et al. | |
| 8,043,207 B2 | 10/2011 | Adams | |
| 8,066,167 B2 | 11/2011 | Measamer et al. | |
| 8,066,169 B2 | 11/2011 | Viola | |
| 8,070,035 B2 | 12/2011 | Holsten et al. | |
| 8,070,037 B2 | 12/2011 | Csiky | |
| 8,109,426 B2* | 2/2012 | Milliman et al. | 227/175.1 |
| 8,123,103 B2* | 2/2012 | Milliman | 227/179.1 |
| 8,322,589 B2* | 12/2012 | Boudreaux | 227/175.4 |
| 8,408,439 B2* | 4/2013 | Huang et al. | 227/175.1 |
| 2003/0111507 A1 | 6/2003 | Nunez | |
| 2005/0051597 A1 | 3/2005 | Toledano | |
| 2005/0107813 A1 | 5/2005 | Gilete Garcia | |
| 2005/0125009 A1 | 6/2005 | Perry et al. | |
| 2005/0145674 A1 | 7/2005 | Sonnenschein et al. | |
| 2005/0145675 A1 | 7/2005 | Hartwick et al. | |
| 2006/0000869 A1 | 1/2006 | Fontayne | |
| 2006/0011698 A1 | 1/2006 | Okada et al. | |
| 2006/0047307 A1 | 3/2006 | Ortiz et al. | |
| 2006/0144897 A1 | 7/2006 | Jankowski et al. | |
| 2006/0201989 A1 | 9/2006 | Ojeda | |
| 2006/0241692 A1 | 10/2006 | McGuckin, Jr. et al. | |
| 2007/0027473 A1 | 2/2007 | Vresh et al. | |
| 2007/0029363 A1 | 2/2007 | Popov | |
| 2007/0060952 A1 | 3/2007 | Roby et al. | |
| 2009/0230170 A1 | 9/2009 | Milliman | |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2009/0255976 A1 | 10/2009 | Marczyk et al. | |
| 2009/0302089 A1 | 12/2009 | Harari et al. | |
| 2010/0001037 A1 | 1/2010 | Racenet et al. | |
| 2010/0019016 A1 | 1/2010 | Edoga et al. | |
| 2010/0038401 A1 | 2/2010 | Milliman et al. | |
| 2010/0051668 A1 | 3/2010 | Milliman et al. | |
| 2010/0065607 A1 | 3/2010 | Orban, III et al. | |
| 2010/0084453 A1 | 4/2010 | Hu | |
| 2010/0089971 A1 | 4/2010 | Milliman et al. | |
| 2010/0108739 A1 | 5/2010 | Holsten et al. | |
| 2010/0108740 A1 | 5/2010 | Pastorelli et al. | |
| 2010/0108741 A1 | 5/2010 | Hessler et al. | |
| 2010/0133319 A1 | 6/2010 | Milliman et al. | |
| 2010/0147923 A1 | 6/2010 | D'Agostino et al. | |
| 2010/0163598 A1 | 7/2010 | Belzer | |
| 2010/0170932 A1 | 7/2010 | Wenchell et al. | |
| 2010/0224668 A1 | 9/2010 | Fontayne et al. | |
| 2010/0230465 A1 | 9/2010 | Smith et al. | |
| 2010/0230466 A1 | 9/2010 | Criscuolo et al. | |
| 2010/0230467 A1 | 9/2010 | Criscuolo et al. | |
| 2010/0258611 A1 | 10/2010 | Smith et al. | |
| 2010/0264195 A1 | 10/2010 | Bettuchi | |
| 2010/0270356 A1 | 10/2010 | Holsten et al. | |
| 2010/0282815 A1 | 11/2010 | Bettuchi et al. | |
| 2010/0301098 A1 | 12/2010 | Kostrzewski | |
| 2010/0327041 A1 | 12/2010 | Milliman et al. | |
| 2011/0006100 A1 | 1/2011 | Milliam | |
| 2011/0006102 A1 | 1/2011 | Kostrzewski | |
| 2011/0011916 A1 | 1/2011 | Levine | |
| 2011/0017800 A1 | 1/2011 | Viola | |
| 2011/0024476 A1 | 2/2011 | Bettuchi et al. | |
| 2011/0024481 A1 | 2/2011 | Bettuchi et al. | |
| 2011/0036889 A1 | 2/2011 | Heinrich et al. | |
| 2011/0036894 A1 | 2/2011 | Bettuchi | |
| 2011/0042442 A1 | 2/2011 | Viola et al. | |
| 2011/0042443 A1 | 2/2011 | Milliman et al. | |
| 2011/0057016 A1 | 3/2011 | Bettuchi | |
| 2011/0089219 A1 | 4/2011 | Hessler | |
| 2011/0095067 A1 | 4/2011 | Ohdaira | |
| 2011/0095068 A1 | 4/2011 | Patel | |
| 2011/0095069 A1 | 4/2011 | Patel et al. | |
| 2011/0095070 A1 | 4/2011 | Patel et al. | |
| 2011/0101065 A1 | 5/2011 | Milliman | |
| 2011/0114697 A1 | 5/2011 | Baxter, III et al. | |
| 2011/0114698 A1 | 5/2011 | Baxter, III et al. | |
| 2011/0114699 A1 | 5/2011 | Baxter, III et al. | |
| 2011/0114700 A1 | 5/2011 | Baxter, III et al. | |
| 2011/0114701 A1 | 5/2011 | Hessler | |
| 2011/0118761 A1 | 5/2011 | Baxter, III et al. | |
| 2011/0130788 A1 | 6/2011 | Orban, III et al. | |
| 2011/0139852 A1 | 6/2011 | Zingman | |
| 2011/0139853 A1 | 6/2011 | Viola | |
| 2011/0144640 A1 | 6/2011 | Heinrich et al. | |
| 2011/0147432 A1 | 6/2011 | Heinrich et al. | |
| 2011/0147434 A1 | 6/2011 | Hueil et al. | |
| 2011/0147435 A1 | 6/2011 | Heinrich et al. | |
| 2011/0192882 A1 | 8/2011 | Hess et al. | |
| 2011/0210156 A1 | 9/2011 | Smith et al. | |
| 2011/0220703 A1 | 9/2011 | Orban, III | |
| 2011/0248067 A1 | 10/2011 | Takei | |
| 2014/0367444 A1* | 12/2014 | Williams | 227/175.1 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| WO | WO 8706448 A | 11/1987 |
| WO | WO 8900406 A1 | 1/1989 |
| WO | WO 9006085 A1 | 6/1990 |

* cited by examiner

EEA TILT TOP ANVIL WITH RATCHET/LOCKING MECHANISM

BACKGROUND

1. Technical Field

The present disclosure relates generally to an anvil assembly which is suitable for use with a circular anastomosis stapler. More specifically, the present disclosure relates to an anvil assembly having a tiltable head which is suitable for use with a circular anastomosis stapler.

2. Description of Related Art

Circular anastomosis staplers which include an anvil assembly having a tiltable anvil head are known in the art. Such tiltable anvil heads have been disclosed in U.S. Publication No. 2010/0038401 to Milliman and U.S. Publication No. 2008/0230581 to Marczyk, the contents of which are incorporated herein by reference in their entirety. The tiltable anvil head normally includes a spring loaded tilting mechanism which tilts the anvil head to its maximum rotation degree as allowed by the stapler geometry. For instance, the tiltable anvil head normally has an operative position at which the anvil head is generally perpendicular to the axis of the stapler, and a fully tilted position at which the anvil head is generally aligned with the axis of the stapler. The tiltable anvil head is pivotable from the operative position to the fully tilted position, but is not able to be maintained at any intermediate positions therebetween. Currently, if excess tissues are placed under the anvil, e.g., when the anvil is manipulated through the colon/bowel or through the anastomotic ring, the excess tissue can inhibit the anvil from being tilted to its maximum rotation degree.

Based on the foregoing, a need still exists for an anvil head that may be partially tilted and maintained at an intermediate position between the operative and fully tilted positions.

SUMMARY

The present disclosure features a tilt anvil assembly for incrementally pivoting an anvil in discrete steps between a non-tilted position and a fully tilted position.

One aspect of the present disclosure features a tilt anvil assembly including a center rod and a head assembly. The head assembly includes a housing, a post, and an anvil plate having staple deforming pockets. The head assembly is pivotally secured to the center rod and pivotal in relation to the center rod in discrete steps between a non-tilted position and a fully tilted position.

The head assembly may have a plurality of partially tilted positions relative to the center rod between the non-tilted position and the fully tilted position. The head assembly may be configured to maintain a partially tilted position.

In another aspect of the present disclosure, the tilt anvil assembly includes a center rod assembly which further includes a collar member having a spring member hingedly attached thereto. The tilt anvil assembly also includes a head assembly which has a housing, a post, and an anvil plate having staple deforming pockets. The head assembly being pivotally secured to the center rod and pivotal in relation to the center rod between a non-tilted position and a fully tilted position. The post includes a plurality of teeth at least partially along one side thereof. The spring member of the collar member is configured to selectively engage the teeth of the post during pivotal movement of the head assembly.

Another aspect of the present disclosure features a method for pivoting an anvil head assembly of a surgical anvil assembly including the steps of: providing an anvil assembly including a rod and a head assembly pivotally secured to the rod. The head assembly is movable between a non-tilted operative position and a fully tilted position via a plurality of partially tilted positions. The method also includes locking the head assembly in a partially tilted position.

DESCRIPTION OF THE DRAWINGS

Various embodiments of the presently disclosed tilt anvil assembly are disclosed herein with reference to the drawings wherein.

DETAILED DESCRIPTION OF EMBODIMENTS

Embodiments of the presently disclosed anvil assembly will now be described in detail with reference to the drawings in which like reference numerals designate identical or corresponding elements in each of the several views. Throughout this description, the term "proximal" will refer to the portion of the instrument closest to the operator and the term "distal" will refer to the portion of the instrument furthest from the operator.

Figure 1:
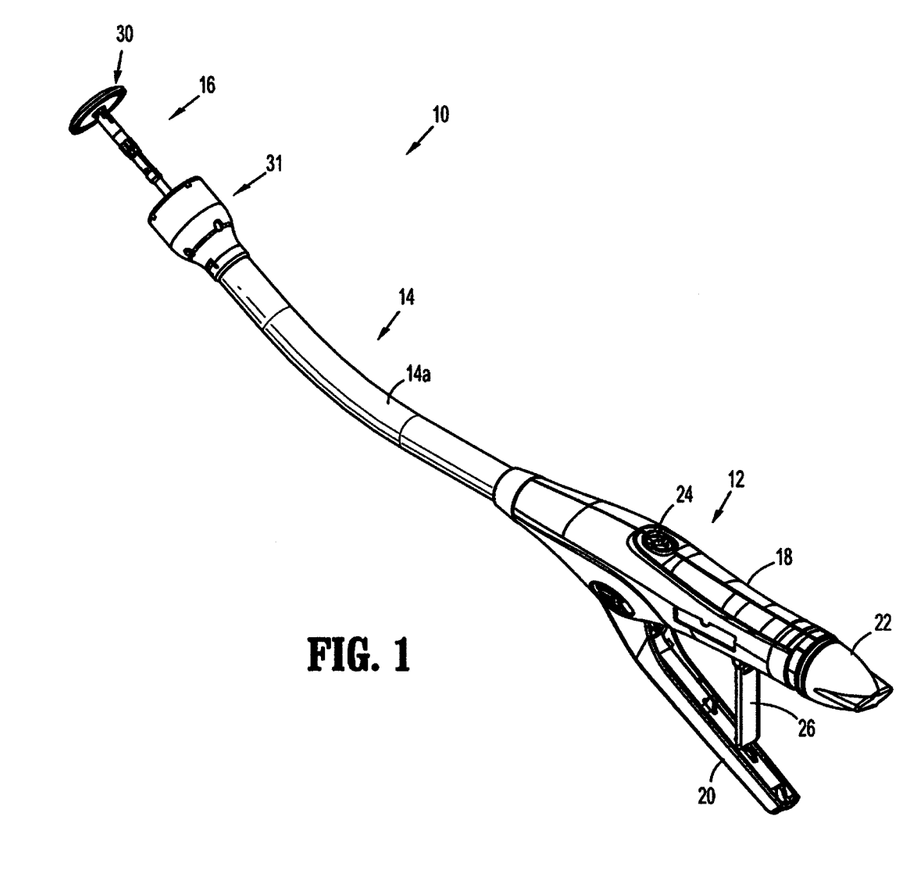
FIG. 1 is a perspective view of a surgical stapling device including an embodiment of an anvil assembly according to the present disclosure.

FIG. 1 illustrates an embodiment of a surgical stapling device configured for use with a tilt anvil assembly according to the present disclosure. Briefly, surgical stapling device 10 includes a proximal handle assembly 12, an elongated central body portion 14 including a curved elongated outer tube 14a, and a distal head portion 16. Alternately, in some surgical procedures, e.g., the treatment of hemorrhoids, it is desirable to have a substantially straight, shortened, central body portion. The length, shape and/or the diameter of body portion 14 and distal head portion 16 may also be varied to suit a particular surgical procedure.

With reference still to FIG. 1, handle assembly 12 includes a stationary handle 18, a firing trigger 20, a rotatable approximation knob 22 and an indicator 24. A pivotally mounted trigger lock 26 is fastened to handle assembly 12 and is manually positioned to prevent inadvertent firing of stapling device 10. Indicator 24 is positioned on the stationary handle 18 and includes indicia, e.g., color coding, alpha-numeric labeling, etc., to identify to a surgeon whether the device is approximated and is ready to be fired. Head portion 16 includes an anvil assembly 30 and a shell assembly 31. For a more detailed discussion of surgical stapler 10, please refer to U.S. Pat. No. 7,431,191 ("the '191 patent") to Milliman, the contents of which are incorporated herein by reference in its entirety.

Figure 2:
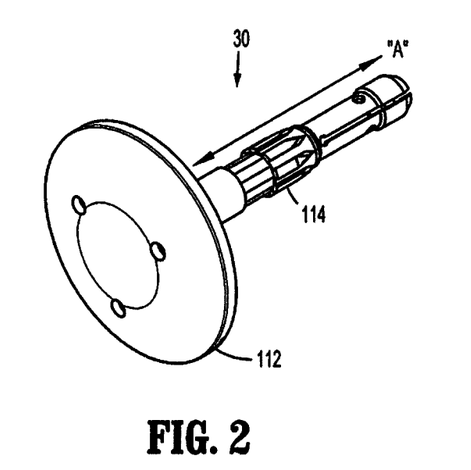
FIG. 2 is a front perspective view of the presently disclosed tilt anvil assembly with the anvil head untilted.
Figure 3:
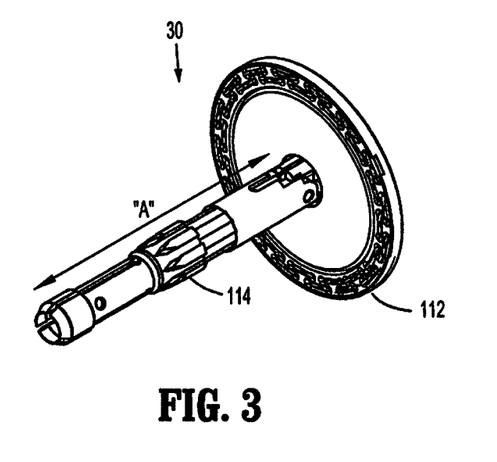
FIG. 3 is a rear perspective view of the tilt anvil assembly shown in FIG. 2.

Referring now to FIGS. 2-17, an embodiment of the present disclosure is shown generally as anvil assembly 30. As illustrated in FIGS. 2-3, the anvil assembly 30 includes a head assembly 112 and a center rod assembly 114 which defines an axis "A" along its length. The anvil assembly 30 has a non-titled or operative position, at which the head assembly 112 is generally perpendicular to the center rod assembly 114. The anvil assembly 30 also has a fully tilted position, at which the head assembly 112 is substantially coaxially aligned with respect to the center rod assembly 114, as shown in FIG. 14. The head assembly 112 is pivotable with respect to the center rod assembly 114 between the non-tilted position and the fully tilted position.

Figure 4:
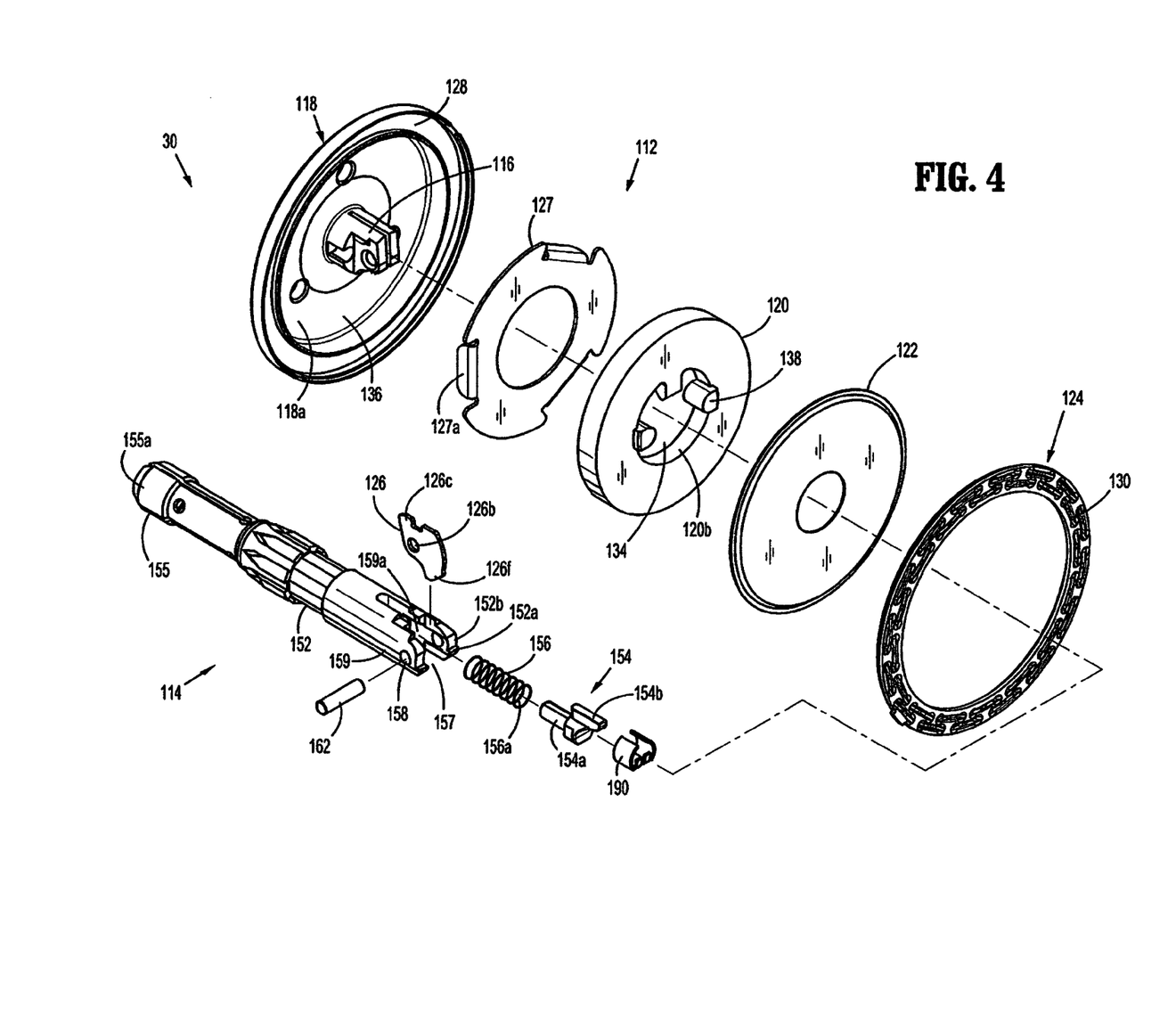
FIG. 4 is a perspective view, with parts separated, of the tilt anvil assembly shown in FIG. 2.

With reference to FIG. 4, the head assembly 112 includes a post 116, a housing 118, a backup member or plate 120, a cutting ring cover 122 that covers a cutting ring (not shown), an anvil plate 124 having staple deforming pockets 130, a cam latch member 126, and a retainer member 127.

Figures 5, 6, 7:
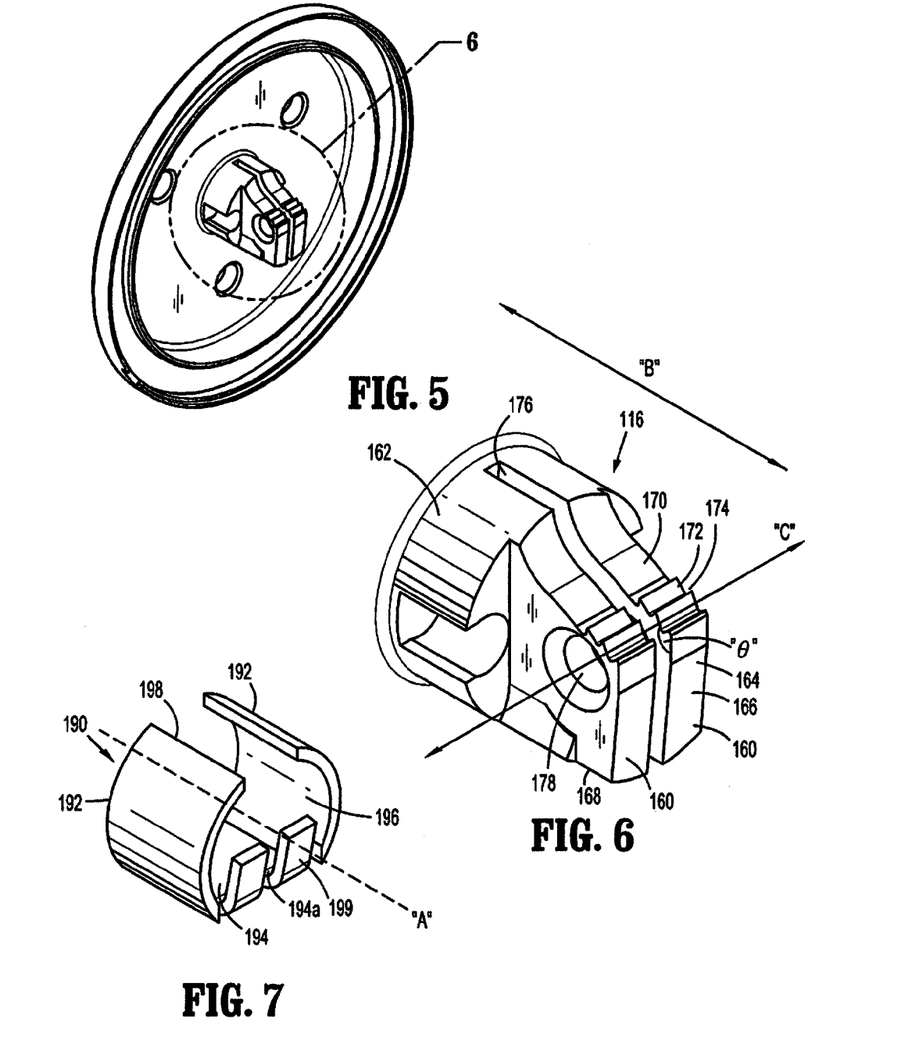
FIG. 5 is a perspective view of the head assembly of the tilt anvil assembly shown in FIG. 3.
FIG. 6 is an enlarged view of the area 6 indicated in FIG. 5.
FIG. 7 is a perspective view of the collar member of the tilt anvil assembly.

With reference to FIGS. 5-6, the post 116 defines an axis "B" along its length. When the anvil assembly 30 is in its non-tilted, operative position, the axis "B" is generally aligned with respect to the axis "A" of the center rod assembly 114. The post 116 includes two support members 160 symmetrically arranged with respect to each other. Each support member 160 includes a distal end 162 which may be monolithically formed with and centrally positioned within housing 118 of the head assembly 112, or may be fastened to the housing 118 using a known fastening technique, e.g., welding. Each support member 160 also includes a proximal end 164 having a planar surface 166, which is generally perpendicular to the axis "B" of the post 116. Furthermore, the post 116 includes a first side surface 168 extending between the distal end 162 and the proximal end 164. The first side surface 168 is generally parallel to the axis "B," and perpendicular to the planar surface 166.

With continued reference to FIGS. 5-6, the post 116 also includes a second side surface 170 diametrically opposed to the first side surface 168. The side surface 170 defines a curved profile, generally inclined with respect to the axis "B" of the post 116. In one example as illustrated in FIG. 6, the second side surface 170 defines an obtuse angle "θ" with respect to the planar surface 166 at the proximal end 164. The side surface 170 may include interlocking ratchet features. For instance as illustrated in FIG. 6, the side surface 170 includes a plurality of teeth 172 disposed immediately adjacent to the proximal end 164 of the post 116 and at least partially along the length of the side surface 170. A notch 174 exists between each pair of adjacent teeth 172. Each tooth 172 extends in a direction traverse or perpendicular to the lengthwise direction of the side surface 170.

The support members 160 are laterally spaced apart from each other with a transverse slot 176 defined therebetween. The transverse slot 176 is dimensioned to receive the cam latch member 126 therein. Further, the support members 160 define a pair of transverse throughbores 178 axially aligned with respect to a pivotal axis "C", and the cam latch member 126 defines a throughbore 126b, such that when the cam latch member 126 is disposed within the transverse slot 176, the throughbores 178 and 126b are coaxially aligned along the pivotal axis "C".

With reference to FIG. 4, the center rod assembly 114 includes a center rod 152, a plunger 154, a plunger spring 156 and a collar member 190. The center rod assembly 114 includes a first end 155 defining a bore 155a therein dimensioned to releasably engage an anvil retainer (not shown) of the surgical stapling device 10. One such surgical stapling device having an anvil retainer and with which the anvil assembly 30 may be used is disclosed in the '191 patent. The center rod assembly 114 also includes a second end 157 having a pair of arms 159 which define a cavity 159a dimensioned to accommodate the plunger 154, the plunger spring 156, the collar member 190, the post 116 of the head assembly 112, and the cam latch member 126 therein.

The center rod 152 defines a pair of throughbores 158. When the post 116 and the cam latch member 126 are positioned within the cavity 159a, the throughbores 158, 178 and 126b of the center rod 152, the post 116 and the cam latch member 126, respectively, are coaxially aligned along the axis "C", and a pivot member 126 is disposed through the throughbores 158, 178 and 126b. As such, the cam latch member 126 is pivotally mounted within the transverse slot 172 of the post 116 about the pivotal axis "C", and the post 116 is pivotally secured to the center rod 152 about the pivotal axis "C", which, in turn, causes the head assembly 112 to be pivotally mounted to the center rod assembly 114 about the pivotal axis "C."

When assembled, the plunger 154, the plunger spring 156 and the collar member 190 are together disposed with the cavity 159a, proximally with respect to the post 116 and the cam latch member 126. The plunger 154 includes a cylindrical main body 154a dimensioned to be disposed in a longitudinal port 156a defined by the plunger spring 156. The plunger 154 also includes an engagement finger 154b extending distally beyond the plunger spring 156. The engagement finger 154b is offset from the pivotal axis "C" of the post 116, and is biased into engagement with an edge 126c of the cam latch 126. Engagement of finger 154b with edge 126c of cam latch 126 presses a leading portion of edge 126f against an inner periphery of the backup plate 120 to urge the head assembly 112 to an operative or non-tilted position on the center rod 152.

The collar member 190 is distally mounted over the plunger 154, and disposed between the plunger 154 and the post 116 when assembled. As illustrated in FIG. 7, the collar member 190 exhibits a generally annular configuration, including two "C"-shaped walls 192 which are diametrically opposed and spaced apart from each other. The collar member 190 further includes a planar wall 194 interconnecting the two "C"-shaped walls 192. The collar member 190 defines a longitudinal opening 196 therethrough and a side opening 198 dimensioned to accommodate the engagement finger 154b of the plunger 154 therein. The collar member 190 further includes two spring members 199 hingedly attached to a distal end 194a of the planar wall 194. The spring members 199 extend radially inwardly towards the axis "A" of the center rod assembly 114. It is envisioned that the spring members 199 are made of deformable, elastic or resilient materials, such that the spring members 199 may be biased relative to the planar wall 194 when placed under pressure, and may resume their original shape and configuration upon removal of the pressured.

The anvil assembly 30 includes a locking mechanism that limits tilting of the head assembly 112 relative to the center rod assembly 114, and secures the anvil assembly 30 in the non-tilting position. Specifically, as illustrated in FIG. 4, the backup plate 120 of the head assembly 112 includes a pair of fingers 138 protruding radially inwardly towards a central opening 134 defined therein. The center rod 152 includes protrusions 152a extending from a distal surface 152b thereof. The protrusions 152a and the distal surface 152b are configured to selectively engage the fingers 138 of the backup plate 120 to inhibit the head assembly 112 from pivoting about the center rod assembly 114.

Figure 8:
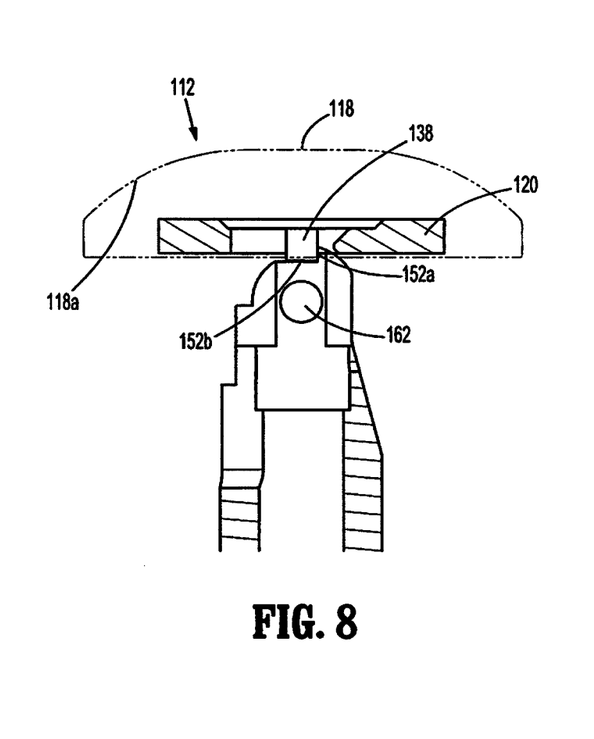
FIG. 8 is a side cross-sectional, schematic view of the tilt anvil assembly shown in FIG. 2 with the anvil head in a locked, non-tilted position.

As illustrated in FIG. 8, before firing the stapling device 10 to advance surgical staplers into tissue, the head assembly 112 is in a pre-fired non-tilted position, in which fingers 138 formed on the backup plate 120 engage protrusions 152a adjacent the distal surface 152b of the center rod 152 to inhibit head assembly 112 from pivoting about the pivot member 162. When the anvil assembly 30 is in its pre-fired non-tilted position, the backup plate 120 is spaced from the backwall 118a of the housing 118 by retainer 127.

Figure 9:
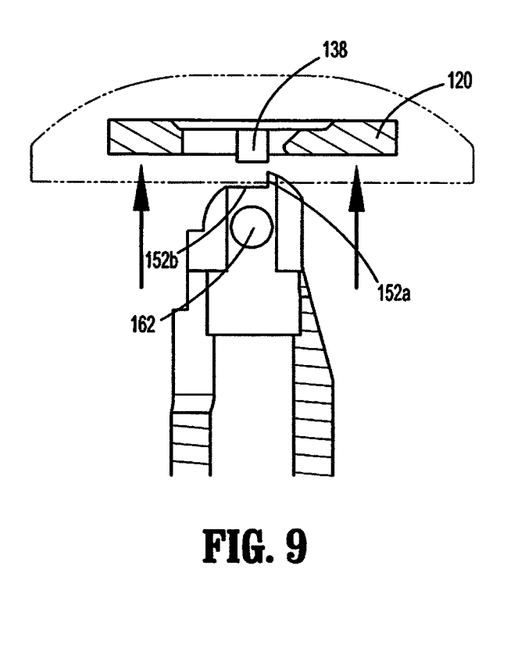
FIG. 9 is a side cross-sectional, schematic view of the tilt anvil assembly shown in FIG. 2 with the anvil head in an unlocked, non-tilted position.

With reference to FIGS. 4 and 9, the firing of surgical stapling device 10 causes a knife blade (not shown) to engage a cutting ring (not shown) to move the cutting ring and the backup plate 120 into annular recess 136 of housing 118 of the head assembly 112. When such movement occurs, deformable tabs 127a of retainer 127 are deformed against the backwall 118a of housing 118 and fingers 138 of the backup member 120 move away from protrusions 152b of center rod 152, unlocking the head assembly 112 from its non-tilted position. Further, inner periphery 120b of backup plate 120 moves past edge 126f of cam latch member 126 such that cam latch member 126 is urged to pivot about pivot member 162 by plunger 154. Engagement of plunger 154 with cam latch member 126 and subsequently with the post 116 urges the head assembly 112 to tilt as illustrated in FIGS. 10-17.

It is noted that the head assembly 112 will not immediately tilt upon firing of a stapling device 10 because, upon firing, the head assembly 112 is in an approximated position, i.e., the anvil head assembly 112 is in close alignment with the shell assembly 31 of the stapling device 10. As such, the head assembly 112 will only begin to tilt when the head assembly 112 and the shell assembly 31 of the stapling device 10 are being unapproximated.

With reference to FIGS. 10-17, subsequent to firing, and when the head assembly 112 and the shell assembly 31 are sufficiently unapproximated, the plunger 154 interacts with the post 116 to incrementally tilt the head assembly 112 from the non-tilted position to the fully titled position.

Figure 10:
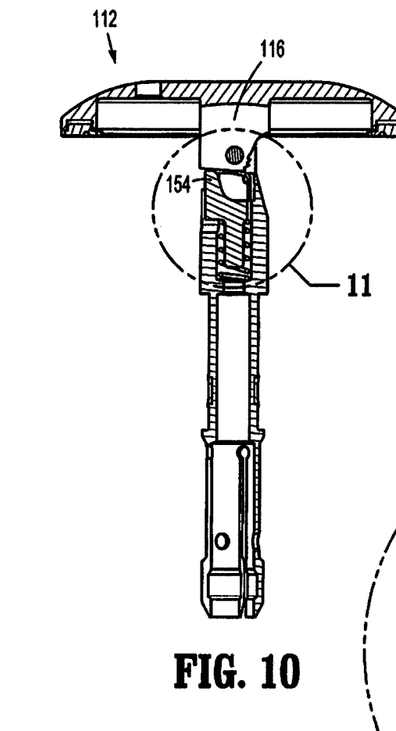
FIG. 10 is a side cross-sectional view of the tilt anvil assembly shown in FIG. 2 with the anvil head in an unlocked, non-tilted position.
Figure 11:
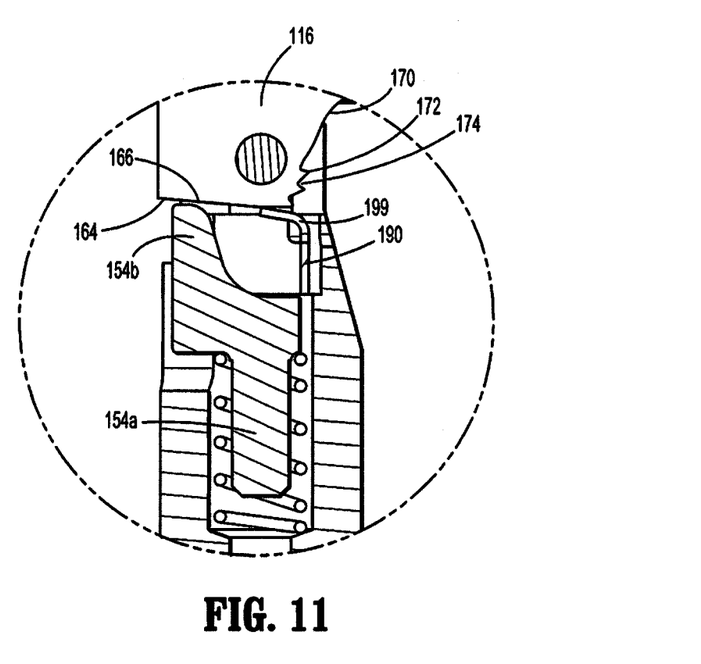
FIG. 11 is an enlarged view of the area 11 indicated in FIG. 10.

FIGS. 10-11 illustrate the anvil assembly 30 in a post-firing non-tilted position, at which the spring member 199 abuts the proximal end 164 of the post 116, lying against the planar surface 164 of the post 116.

FIGS. 12-17 illustrate that as the plunger 154 urges the post 116 to pivot about the pivotal axis "C", the spring member 199 passes up and over each tooth 172 along the side surface 170 of the post 116. After an appropriate tilting angle is reached, the spring member 199 locks against a notch 174 to maintain the head assembly 112 at the desired tilting position. Each notch 174 represents a tilted position of the head assembly 112 at a particular rotation angle relative to the center rod assembly 114. The interlocking ratchet features of the anvil assembly 30, i.e., the teeth 172 and notches 174 of the post 116 and the spring member 199 of the collar member 190, enables incremental pivotal movement of the head assembly 112 relative to the center rod assembly 114 in discrete steps. By selectively engaging and/or disengaging the notches 174 along the side surface 170 of the post 116, the spring member 199 provides locking mechanism to selectively maintain the head assembly 112 at any partially tilted position.

Figure 12:
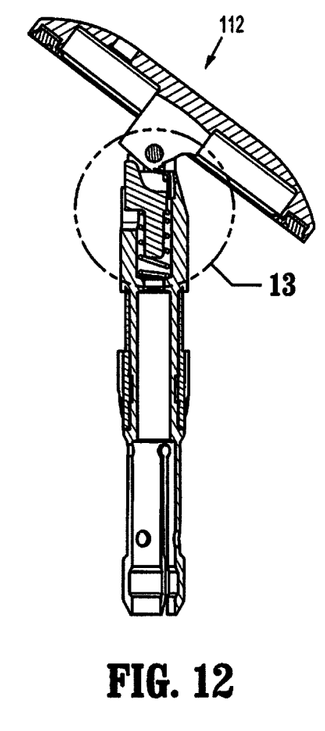
FIG. 12 is a side cross-sectional view of the tilt anvil assembly shown in FIG. 2 with the anvil head in a partially tilted position.
Figure 13:
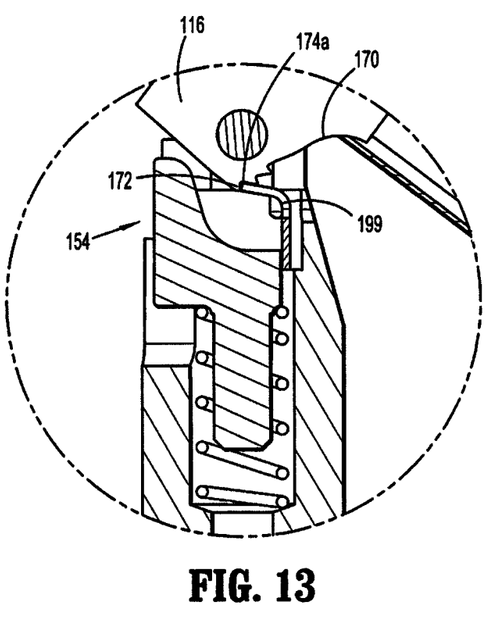
FIG. 13 is an enlarged view of the area 13 indicated in FIG. 12.
Figure 14:
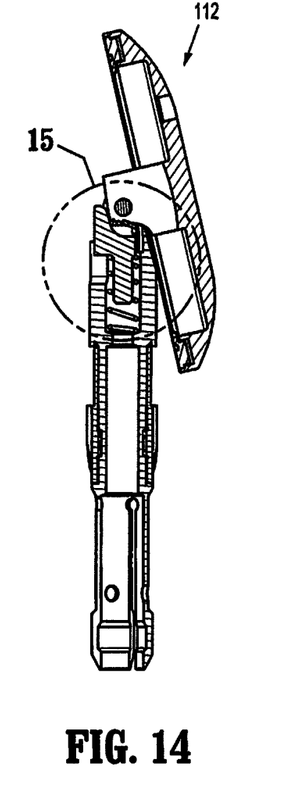
FIG. 14 is a side cross-sectional view of the tilt anvil assembly shown in FIG. 2 with the anvil head in a fully tilted position.
Figure 15:
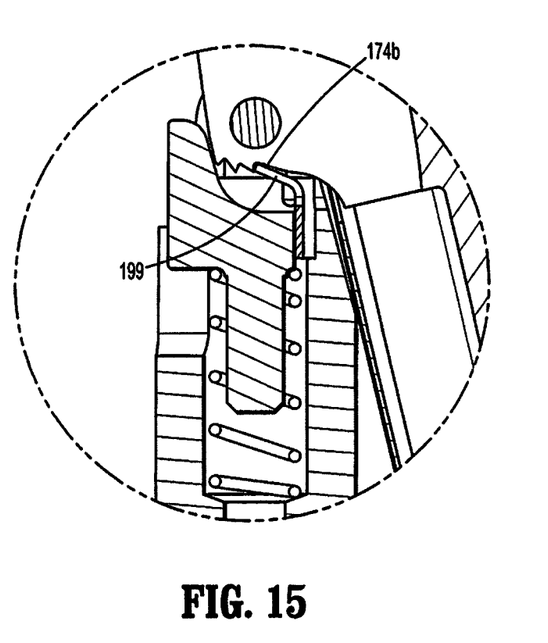
FIG. 15 is an enlarged view of the area 15 indicated in FIG. 14.
Figure 16:
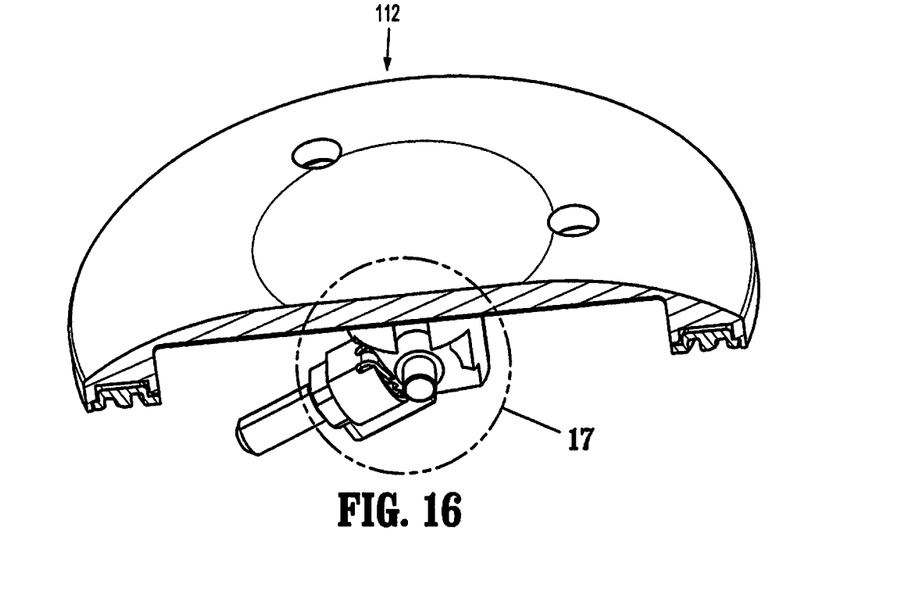
FIG. 16 is a cut-away view of the tilt anvil assembly shown in FIG. 14.
Figure 17:
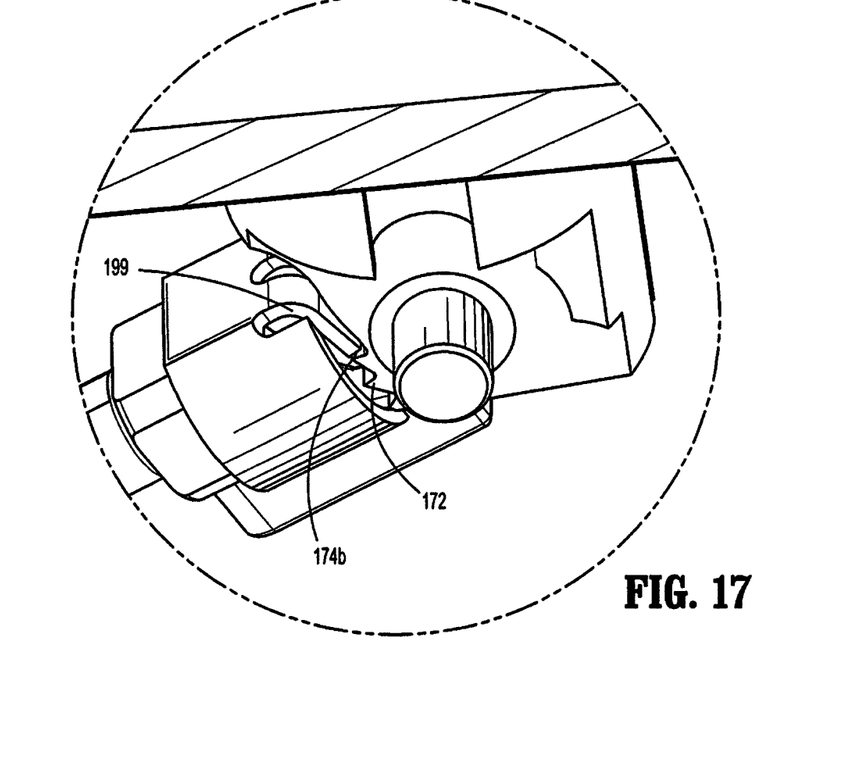
FIG. 17 is an enlarged view of the area 17 indicated in FIG. 16.

As illustrated in FIGS. 12-13, the spring member 199 engages a particular notch 174a to maintain a partially tilted position between the non-tilted position and the fully tilted position. FIGS. 14-17 illustrates that the head assembly 112 is in its fully tilted position at which that the spring member 199 engages the distal-most notch 174b of the post 116.

It will be understood that various modifications may be made to the embodiments disclosed herein. The above description should not be construed as limiting, but merely as exemplifications of preferred embodiments. Those skilled in the art will envision other modifications within the scope and spirit of the claims appended hereto.

What is claimed is:

1. A tilt anvil assembly comprising:
   a center rod defining a longitudinal axis; and
   a head assembly including a housing, a post, and an anvil plate having staple deforming pockets, the post including a ratchet mechanism engaging the center rod during pivotal movement of the head assembly, the ratchet mechanism including a plurality of teeth, the head assembly being pivotally secured to the center rod, wherein the plurality of teeth of the ratchet mechanism engage the center rod to selectively maintain an off-axis angular orientation of the head assembly in relation to the longitudinal axis of the center rod in increments between a non-tilted position and a fully tilted position.

2. The tilt anvil assembly according to claim 1, wherein the head assembly is transitionable to a plurality of partially tilted positions relative to the longitudinal axis of the center rod between the non-tilted position and the fully tilted position.

3. The tilt anvil assembly according to claim 1, wherein the center rod further includes a collar member configured to selectively engage the post during pivotal movement of the post.

4. The tilt anvil assembly according to claim 3, wherein the post includes a side surface defining a curved profile and forming an obtuse angle with respect to a proximal surface of the post.

5. The tilt anvil assembly according to claim 4, wherein the plurality of teeth of the ratchet mechanism are disposed, at least partially, along a length of the side surface, and each tooth extends in a direction perpendicular to a lengthwise direction of the side surface.

6. The tilt anvil assembly according to claim 5, wherein the side surface includes a notch between each pair of adjacent teeth.

7. The tilt anvil assembly according to claim 3, wherein the collar member includes a spring member configured to selectively engage the post.

8. The tilt anvil assembly according to claim 7, wherein the spring member comprises deformable, elastic and resilient materials.

9. A tilt anvil assembly comprising:
   a center rod assembly including a collar member having a spring member hingedly attached thereto, the center rod assembly defining a longitudinal axis; and
   a head assembly including a housing, a post, and an anvil plate having staple deforming pockets, the head assembly being pivotally secured to the center rod assembly and pivotal in relation to the longitudinal axis of the center rod assembly between a non-tilted position and a fully tilted position, the post including a plurality of teeth disposed at least partially along one side thereof;

wherein the spring member of the collar member is configured to selectively engage the teeth of the post during pivotal movement of the head assembly.

10. The tilt anvil assembly according to claim 9, wherein the head assembly is transitonable to a plurality of partially tilted positions relative to the longitudinal axis of the center rod assembly between the non-tilted position and the fully tilted position.

11. The tilt anvil assembly according to claim 9, wherein the head assembly further includes a pivotal latch member positioned to inhibit movement of the head assembly from the non-tilted position.

12. The tilt anvil assembly according to claim 9, further including a plunger which is urged by a biasing member into engagement with the post to effect pivotal movement of the head assembly relative to the center rod assembly.

13. The tilt anvil assembly according to claim 5, wherein the collar member includes a spring member configured to selectively engage one of the plurality of teeth on the side surface of the post.

14. The tilt anvil assembly according to claim 7, wherein the spring member is configured to selectively engage the plurality of teeth of the ratchet mechanism.

* * * * *